(12) United States Patent
Thorseth

(10) Patent No.: US 9,612,217 B2
(45) Date of Patent: Apr. 4, 2017

(54) ELECTROPLATING BATH ANALYSIS

(71) Applicant: Rohm and Haas Electronic Materials LLC, Marlborough, MA (US)

(72) Inventor: Matthew A. Thorseth, West Minster, MA (US)

(73) Assignee: Rohm and Haas Electronics Materials LLC, Marlborough, MA (US)

( * ) Notice: Subject to any disclaimer, the term of this patent is extended or adjusted under 35 U.S.C. 154(b) by 175 days.

(21) Appl. No.: 14/693,818

(22) Filed: Apr. 22, 2015

(65) Prior Publication Data
US 2015/0300970 A1 Oct. 22, 2015

Related U.S. Application Data

(60) Provisional application No. 61/982,726, filed on Apr. 22, 2014.

(51) Int. Cl.
*G01N 27/02* (2006.01)
*C25D 3/38* (2006.01)
*C25D 21/14* (2006.01)

(52) U.S. Cl.
CPC ............ *G01N 27/026* (2013.01); *C25D 3/38* (2013.01); *C25D 21/14* (2013.01)

(58) Field of Classification Search
CPC ......... G01N 27/026; C25D 3/38; C25D 21/14
See application file for complete search history.

(56) References Cited

U.S. PATENT DOCUMENTS

| 4,812,210 A | 3/1989 | Bonivert et al. |
|---|---|---|
| 5,370,776 A | 12/1994 | Chen |
| 5,755,954 A | 5/1998 | Ludwig et al. |
| 6,508,924 B1 | 1/2003 | Gomez et al. |
| 6,827,839 B2 | 12/2004 | Sonnenberg et al. |
| 7,124,120 B2 | 10/2006 | Wikiel et al. |
| 7,186,326 B2 | 3/2007 | Shalyt et al. |
| 7,427,344 B2 | 9/2008 | Han et al. |
| 2003/0062266 A1 | 4/2003 | Chalyt et al. |
| 2003/0111346 A1 | 6/2003 | Zdunek |
| 2005/0241948 A1 | 11/2005 | Han et al. |
| 2011/0241709 A1 | 10/2011 | Lyu et al. |

FOREIGN PATENT DOCUMENTS

| EP | 1471347 A1 | 10/2004 |
|---|---|---|
| WO | 03029779 A2 | 4/2003 |

OTHER PUBLICATIONS

Search report for corresponding Taiwan Application No. 104112835 dated May 20, 2016.
Gabrielli, et al, "Electrochemical impedance spectroscopy investigation of bath aging in damascene process chemistries", Electrochemical and Solid-State Letters, Jan. 22, 2004, pp. C31, vol. 7, No. 3.
Farmer, et al, "Impedance probe for measuring organic additives in electroplating baths", Plating and Surface Finishing, Aug. 1, 1989, pp. 56-61, vol. 76, No. 8.

(Continued)

*Primary Examiner* — Daniel Miller
(74) *Attorney, Agent, or Firm* — S. Matthew Cairns

(57) ABSTRACT

Electrochemical impedance spectroscopy is used to determine the amount of organic additive in a metal electroplating bath.

9 Claims, 2 Drawing Sheets

Figure 1: Fit of Z'

(56) References Cited

OTHER PUBLICATIONS

Figure 1:
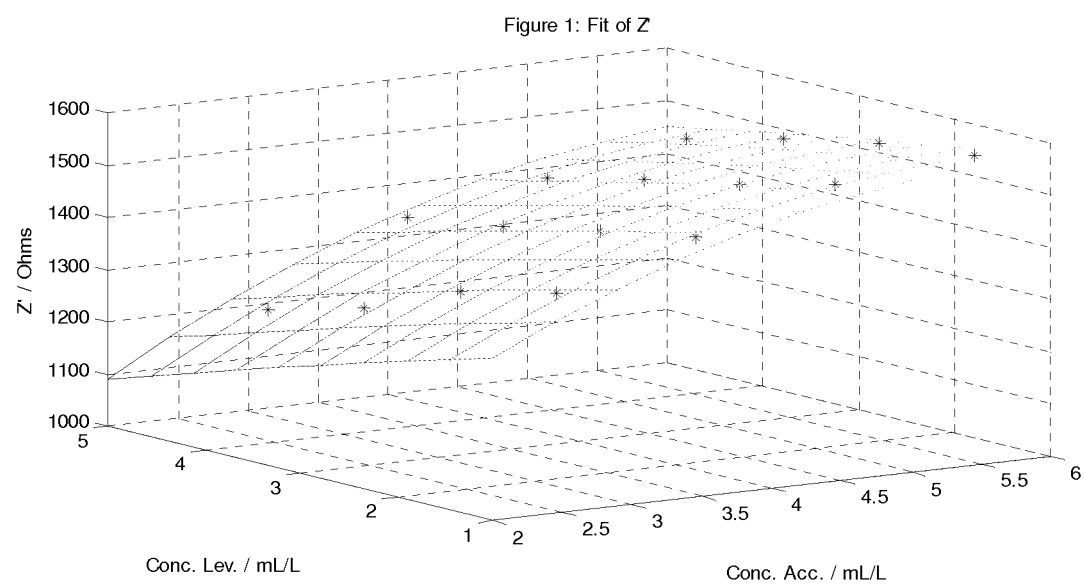

Hung-Min Chen, et al, "An electrochemical impedance spectroscopy study of chloride and 3-marcapto-1-propanesulfonic acid interactions in acidic copper electroplating bath," https://aiche.confex.com/aiche/2005/techprogram/P2489.HTM, Nov. 4, 2005.
Gabrielli, et al, "An investigation of copper interconnect deposition bath ageing by electrochemical impedance spectroscopy", Journal of Applied Electrochemistry, vol. 38, No. 4, pp. 457-468.
Search Report for corresponding European Application No. 15 16 4281 dated Sep. 18, 2015.
Search report for corresponding China Application No. 201510341903.0 dated Dec. 20, 2016.

Apparatus having:
- Rotatable working electrode
- Reference electrode
- Counter electrode in operable communication with the working and reference electrodes
- Potentiostat
- Frequency response analyzer

*Fig. 2*

ELECTROPLATING BATH ANALYSIS

The present invention relates generally to the field of metal electroplating baths, and more particularly to the control of organic additives in metal electroplating baths.

Electroplating is a complex process involving multiple components in an electroplating bath. It is important that the concentration of certain of the components be kept within close tolerances in order to obtain a high quality metal deposit. If the additive content goes too far out of range, the quality of the metal deposit suffers and the deposit may be dull in appearance and/or brittle or powdery in structure. Other possible consequences include low throwing power and/or plating folds with bad leveling. In the copper plating of electronic devices having small features, such as wafers used in the manufacture of integrated circuits, the concentrations of organic additives in the copper plating baths must be maintained within certain limits in order to obtain super-filling, or bottom-up filling.

In some cases, chemical analysis of individual bath constituents can be made regularly (such as pH measurement for acid content) and additions made as required. However, other components such as organic additives cannot be analyzed so easily. The operating concentration of organic additives, such as brighteners, suppressors, and levelers, is low and their quantitative analysis is complicated and subject to error.

Various methods have been used to control the amount of organic additives in metal electroplating baths. One method is simply to make regular additions of the desired organic additives based upon empirical rules established by experience. However, depletion of particular additives is not always constant with time or with bath use. Another known method for plating bath control is to plate articles and visually evaluate the plating quality to determine if the bath is performing satisfactorily. This is a time consuming test which gives at best a rough approximation of the concentration of the constituents of the bath. Conventional copper electroplating bath analysis uses cyclic voltammetric stripping (CVS) or cyclic pulse voltammetric stripping (CPVS) to determine organic additive content. CVS methods take a relatively long time, such as from 2 to 4 hours, to perform for all bath components. CPVS methods are more prone to errors than CVS methods. U.S. Pat. No. 7,427,344 proposed a method for measuring organic additive concentration in a metal electroplating bath based on the double layer capacitance of a working electrode immersed in an electroplating solution using current decay under constant potentials. The method in this patent looks at time dependence of the adsorption/desorption of organic additives one at a time, and has not demonstrated the ability to distinguish one additive from another. This double layer capacitance approach has not gained widespread acceptance. There remains a need for a relatively rapid analysis of organic components in metal electroplating baths.

The present invention provides a method for determining the concentration of one or more organic components in a metal electroplating bath comprising the steps of: a) providing an apparatus having a rotatable working electrode, a counter electrode, a reference electrode, a potentiostat, and a frequency response analyzer, wherein the counter electrode is in operable communication with the working and reference electrodes; b) obtaining a metal electroplating bath solution comprising an unknown quantity of organic additive; c) contacting each of the working electrode, reference electrode and counter electrode with the metal electroplating solution, and cleaning the working electrode surface by applying a positive potential while rotating the working electrode at a first rotation speed; d) equilibrating convection in the electroplating solution by rotating the working electrode at a second rotation speed at open circuit potential; e) applying a potential to the working electrode that is 50 to 500 mV negative of the metal underpotential deposition peak and overlaying an alternating potential perturbation of from 1 to 100 mV; f) measuring an impedance response of the organic additive solution over a frequency range of from 10 kHz to 1 mHz; g) selecting a frequency from the impedance response; and h) determining a concentration of the organic additive by comparing the impedance response at the selected frequency to a calibration curve.

Also provided by the present invention is a method for controlling the concentration of an organic additive in an electroplating bath comprising the steps of: a) determining a quantity of an organic additive as described above; and b) comparing the quantity of organic additive to a preset value; provided that when the concentration of the organic additive falls below the preset value, a control process is activated that increases the concentration of the organic additive to the preset value.

FIG. 1 shows a calibration curve for accelerator and leveler dosing according to the invention. FIG. 2 shows an apparatus for use in the invention.

As used herein, the following abbreviations have the following meanings: Hz=Hertz; mHz=millihertz; kHz=kilohertz; V=Volt; mV=millivolt; mL=milliliter; L=liter; cm=centimeter; rpm=rotation per minute; sec.=second; and min.=minute. All numerical ranges are inclusive and combinable in any order, except where it is clear that such numerical ranges are constrained to add up to 100%. The articles "a", "an" and "the" refer to the singular and the plural.

The present invention uses electrochemical impedance spectroscopy to determine the concentration of one or more organic additives (components) in a metal electroplating bath (or solution) comprising the steps of: a) providing an apparatus shown in FIG. 2 having a rotatable working electrode, a counter electrode, a reference electrode, a potentiostat, and a frequency response analyzer, wherein the counter electrode is in operable communication with the working and reference electrodes; b) obtaining a metal electroplating bath solution comprising an unknown quantity of organic additive; c) contacting each of the working electrode, reference electrode and counter electrode with the metal electroplating solution, and cleaning the working electrode surface by applying a positive potential while rotating the working electrode at a first rotation speed; d) equilibrating convection in the electroplating solution by rotating the working electrode at a second rotation speed at open circuit potential; e) applying a potential to the working electrode that is 50 to 500 mV negative of the metal underpotential deposition peak and overlaying an alternating potential perturbation of from 1 to 100 mV; f) measuring an impedance response of the organic additive solution over a frequency range of from 10 kHz to 1 mHz; g) selecting a frequency from the impedance response; and h) determining a concentration of the organic additive by comparing the impedance response at the selected frequency to a calibration curve. This method relies on the fact that differently sized organic additives will respond differently to different frequencies. A relatively larger organic additive will not respond as quickly to a small change in the frequency as will a relatively smaller organic additive. Accordingly, the relative effects of different organic additives can be separated from each other, and the concentrations of these additives determined.

A wide variety of apparatuses may be used with the present invention, provided such apparatus has a rotatable working electrode, a counter electrode, a reference electrode, a potentiostat, and a frequency response analyzer, wherein the counter electrode is in operable communication with the working and reference electrodes. A suitable apparatus is a 100 mL, water-jacketed beaker having a thermostat to control the temperature of the solution being analyzed at 25° C. and equipped with the three electrodes.

The working electrode is a suitable rotating metal disc, which may be composed of a metal chosen from platinum, copper, nickel, chromium, zinc, tin, gold, silver, lead, cadmium, solder, glassy carbon, mercury or stainless steel, and preferably a platinum disc. More preferably, the working electrode is a rotating 0.2 $cm^2$ platinum disc. The working electrode typically has a flat, polished surface, small diameter and may be mounted flush with the end of a Kel-F cylinder. A small diameter disk is preferred since a larger diameter will result in poor sensitivity due to non-uniform current density across the diameter. Typically, the working electrode is connected to a rotator, such as a Pine Instruments MSRX rotator. The reference electrode is conventionally a saturated Calomel reference electrode (SCE) or silver/silver chloride electrode, and is preferably a silver/silver chloride electrode. The counter electrode preferably comprises platinum, and more preferably is a platinum wire.

Any suitable computer is used to control an electronic potentiostat which controls the energy input between the working electrode relative to the reference electrode. Any suitable potentiostat may be used, such as a Metrohm Autolab PGSTAT302N potentiostat. Using a suitable program, the energy input (potential) sequences of the present invention may be applied to the working electrode. A variety of frequency response analyzers may be used. Suitable frequency response analyzers are FRA2 and FRA32M modules, both available from Metrohm Autolab B.V., or alternatively, a computer equipped with frequency analysis software, such as is available from Gamry Instruments.

Typically, the electrodes are cleaned prior to each use. A suitable cleaning step involves immersing the working, reference and counter electrodes in a 10% (v/v) sulfuric acid solution and performing cyclic voltammetry between 1.6 and −0.2 V at 100 mV/sec. When a platinum working electrode and counter electrode are used, such cleaning is continued until a reproducible, clean platinum in sulfuric acid voltammogram is obtained. The cleaned electrodes are then rinsed thoroughly with deionized (DI) water before being placed in a solution to be analyzed.

Metal electroplating baths (or solutions) contain a metal to be plated, usually in the form of a bath soluble metal salt, an electrolyte, one or more organic components (additives), optionally a source of halide, and optionally one or more other components. Various metal electroplating baths may be analyzed according to the present invention, such as electroplating baths used to deposit copper, nickel, tin, silver, gold, indium, or alloys thereof. It is preferred that the present method is used to determine the concentration of organic additives in a copper electroplating bath. The electrolyte may be alkaline or acidic, depending upon the particular metal electroplating bath used, and is preferably acidic. For example, copper electroplating baths are typically acidic, having a pH of <2. Many organic additives are used in metal electroplating baths, such as, but not limited to, accelerators, suppressors, levelers, conductivity enhancers, and the like. Accelerators, also called brighteners, brightening agents or gloss controlling agents, function to increase the metal plating rate. Suppressors function to decrease the metal plating rate. Levelers, also referred to as leveling agents, have suppressive properties and function to provide a level metal deposit over a substrate surface. Preferably, the present method determines the concentration of one or more organic additives chosen from accelerators, suppressors or levelers. The concentration of one or more of accelerators, suppressors and levelers in a copper electroplating bath is more preferably determined according to the present method.

A portion of an electroplating solution containing an organic additive to be analyzed (the analyte) is added to the apparatus, and the working, reference and counter electrodes are contacted with the solution. The apparatus typically maintains the solution to be analyzed at a set temperature, such as at 25° C. The working electrode surface is then cleaned using the solution to be analyzed by applying a positive potential for a period of time while rotating the working electrode at a first rotation speed. Any suitable positive potential may be used, and the selection of such potential is well within the ability of those skilled in the art. A suitable range of potentials is from 1.2 V to 2.0 V. For example, when a copper electroplating solution is being analyzed, a suitable potential is 1.6 V. Such potential is applied for a suitable time period to clean the electrode surface. The time period is not critical. A suitable time period is from 0.01 to 120 seconds, preferably from 1 to 60 seconds, and more preferably from 1 to 45 seconds. The first rotation speed is not critical, however rotating the electrode sufficiently is effective to remove bubbles from the electrode surface. Typically, the first rotation speed is from 100 to 2500 rpm, and preferably from 500 to 1500 rpm, although slower or faster rotation speeds may be used.

Next, the working electrode is set to open circuit potential and rotated at a second rotation speed for a period of time sufficient to allow solution convection to equilibrate. Open circuit potential is the potential of the working electrode relative to the reference electrode when no potential is applied to the system. Any suitable rotation speed may be selected as the second rotation speed. Typical second rotation speeds are from 1 to 4000 rpm, preferably from 1 to 3500 rpm, and more preferably from 1 to 3000 rpm. The second rotation speed may be the same as, or different from, the first rotation speed. Preferably, the second rotation speed is slower than the first rotation speed. Lower second rotation speeds result in less convection to the electrode and select for relatively lower molecular weight species with relatively higher diffusion coefficients. Higher second rotation speeds result in more convection and select for relatively higher molecular weight species with relatively higher diffusion coefficients. The time period for this equilibration step is not critical, and may vary from 0.01 to 120 seconds, preferably from 1 to 60 seconds, and more preferably from 1 to 45 seconds.

Following the equilibration step, a set potential is applied to the working electrode that is 50 to 500 mV negative of the metal underpotential deposition peak and an alternating perturbation potential of from 1 to 100 mV is overlaid on the applied potential. Underpotential deposition is a phenomenon in electroplating where a metal deposits at a potential less negative than its Nernst equilibrium potential. The determination of a metal underpotential deposition peak is well within the ability of those skilled in the art. When a copper electroplating solution is analyzed using the present method, a potential of 0.0 V relative to the reference electrode is applied. The alternating potential perturbation is typically chosen from a sine wave or a square wave, and is preferably a sine wave. Preferably, the alternating potential perturbation is in the range of from 1 to 50 my, more preferably from 1 to 25 mV, and yet more preferably from 1 to 10 mV. The potential applied in this step is set, that is, it does not vary.

The impedance response of the organic additive is measured over a frequency range of from 10 kHz to 1 mHz. The high end of the frequency range favors bulk solution properties (solution conductivity), while the lower end is additive adsorption onto the electrode double layer. Since the measurement time at each frequency is the inverse of the frequency, lower end frequencies require more time for data collection. Experiment times can be reduced by applying coincident alternating perturbation potentials, that is, applying a high frequency (such as a 1 kHz) signal on top of a lower frequency (such as a 1 Hz) signal and deconvolution through Fourier transformation. Up to 3 alternating perturbation potentials can be applied at the same time. The scanned frequencies are used to construct a Nyquist plot. Impedance is a complex number, where resistance is the real component and the combined capacitance and inductance are the imaginary component. The real and imaginary components of the impedance at various potential amplitudes are fit using MATLAB™ ver. 7.9.0.529 (The Math Works, Inc., Natick, Mass.) software to a second or third order polynomial equation. In a copper electroplating bath containing a brightening agent, a suppressor and a leveling agent, the real component of the impedance is primarily dependent on the accelerator concentration and the imaginary component of the impedance is primarily dependent on the leveler and suppressor concentrations.

A frequency is selected from the range used to correlate the impedance response to the additive concentrations. Alternatively, a plurality of frequencies may be selected, such as two or three or more frequencies. For an organic additive in a copper electroplating bath, a suitable frequency is 1 Hz. The impedance response at the selected frequency (or frequencies) is compared to a calibration curve (or correlative data set) to determine the concentration of the organic additive.

Calibration curves may be obtained by first providing a plurality of calibration solutions, wherein each solution has a known and the same quantity of electrolyte and metal salt, and wherein each solution has a known and different quantity of an organic additive (analyte), such as an accelerator. Each of the calibration solutions is then contacted with the working electrode, reference electrode and counter electrode of the apparatus described above and subjected to the process steps described above. The real and imaginary components of the impedance of each calibration solution at various potential amplitudes are fit using MATLAB™ software to a second or third order polynomial equation. The number of calibration points needed depends on the complexity of the solution, with a more complex solution requiring more data points. If a second organic additive (analyte), such as a leveler, is also to be analyzed, then to each of the above calibration solutions is added a known but different quantity of the second organic additive, to provide a plurality of second calibration solutions. Each second calibration solution is then contacted with the working electrode, reference electrode and counter electrode of the apparatus described above and subjected to the process steps described above. If a third organic additive (analyte), such as a suppressor, is also to be analyzed, then to each of the above second calibration solutions is added a known but different quantity of the third organic additive, to provide a plurality of third calibration solutions. Each third calibration solution is then contacted with the working electrode, reference electrode and counter electrode of the apparatus described above and subjected to the process steps described above.

EXAMPLE 1

Calibration solutions were prepared using by combining an electrolyte containing 60 g/L $Cu^{2+}$ (from $CuSO_4$), 50 g/L (18N $H_2SO_4$), 80 mg/L $Cl^-$ (from 1N HCl), and 8.0 mL/L of suppressor. Four calibration samples were prepared, each having a different amount of accelerator. Each calibration solution was prepared with the amount of accelerator shown in Table 1 and 1.5 mL/L of leveler. After the impedance response was measured for each calibration solution, an additional 1 mL/L of leveler was added to each calibration solution (for a total of 2.5 mL/L of leveler), and the impedance was again measured. This process was repeated two more times, resulting in impedance measurements for calibration solutions having 3.5 and 4.5 mL/L of leveler. The accelerator and total leveler concentrations for each calibration solution are shown in Table 1.

TABLE 1

| Calibration Solution | Accelerator Concentration (mL/L) | Leveler Concentration (mL/L) |
|---|---|---|
| 1 | 2.8 | 1.5, 2.5, 3.5, 4.5 |
| 2 | 3.8 | 1.5, 2.5, 3.5, 4.5 |
| 3 | 4.8 | 1.5, 2.5, 3.5, 4.5 |
| 4 | 5.8 | 1.5, 2.5, 3.5, 4.5 |

Electrochemical experiments were performed using and AUTOLAB PGSTAT302N equipped with an FRA2 module for impedance experiments. Each calibration solution was added to a 100 mL water-jacketed beaker set to maintain a temperature of 25° C. The working electrode was a rotating 0.196 $cm^2$ Pt disc, with a Pt wire counter electrode and a saturated Ag/AgCl counter electrode. The electrodes were thoroughly cleaned in 10% $H_2SO_4$ by cycling the potential between −0.2 and 1.6 V until a reproducible clean Pt in $H_2SO_4$ voltammogram was obtained. The electrodes were then rinsed thoroughly with DI water before being immersed in each calibration solution. Each calibration solution was titrated using 2.0 mL DOSINO™ servomotor controlled buret solution titrator (available from Metrohm).

For each calibration solution, 1.6 V was applied for 30 sec. while rotating the working electrode at 1600 rpm to clean electrode surface. Next, the working electrode was rotated at 25 rpm under open circuit potential for 30 sec. A potential of 0.0 V was then applied, and a 5 mV sine wave was overlaid on top of the controlled potential. The impedance response of the leveler was then measured over a frequency range of 10 kHz to 10 mHz. This process was repeated 2 more times for each calibration solution. To each calibration solution was then added titrated with an additional 1.0 mL/L of the leveler, and the process steps were repeated. FIG. 1 shows calibration curves generated.

Once the data were collected, the values for the real and imaginary components of the impedance for the accelerator and leveler at 1 Hz were fitted to a second order polynomial using a MATLAB™ surface fitting program. The calibrations yielded the following equations:

$$Z'(1\ Hz) = 1410 - 105.7[A] + 202.8[L] + 4.611[A]^2 - 4[A][L] - 11.11[L]^2$$

$$-Z''(1\ Hz)=105-14.63[A]+82.15[L]+0.9949[A]^2-5.28[A][L]-2.204[L]^2$$

where Z' refers to the real component of the impedance, $-Z''$ refers to the imaginary component of the impedance, [A] is the accelerator concentration and [L] is the leveler concentration. These equations then used to solve for the accelerator and leveler concentration of test solutions prepared using the same concentrations as the calibration solutions.

What is claimed is:

1. A method for determining the concentration of one or more organic components in a metal electroplating bath comprising the steps of:
    a) providing an apparatus having a rotatable working electrode, a counter electrode, a reference electrode, a potentiostat, and a frequency response analyzer, wherein the counter electrode is in operable communication with the working and reference electrodes;
    b) obtaining a metal electroplating bath solution comprising an unknown quantity of organic additive;
    c) contacting each of the working electrode, reference electrode and counter electrode with the metal electroplating solution, and cleaning the working electrode surface by applying a positive potential while rotating the working electrode at a first rotation speed;
    d) equilibrating convection in the electroplating solution by rotating the working electrode at a second rotation speed at open circuit potential, wherein the second rotation speed is different from the first rotation speed;
    e) applying a potential to the working electrode that is 50 to 500 mV negative of a metal underpotential deposition peak and overlaying an alternating potential perturbation of from 1 to 100 mV;
    f) measuring an impedance response of the organic additive solution over a frequency range of from 10 kHz to 1 mHz;
    g) selecting a frequency from the impedance response; and
    h) determining a concentration of the organic additive by comparing the impedance response at the selected frequency to a calibration curve.

2. The method of claim 1 wherein the metal is copper.

3. The method of claim 1 wherein the alternating potential perturbation is chosen from a sine wave and a square wave.

4. The method of claim 1 wherein the first rotation speed is faster than the second rotation speed.

5. The method of claim 1 wherein the working electrode is a platinum disc.

6. The method of claim 1 wherein the counter electrode comprises platinum.

7. The method of claim 1 wherein the organic additive is chosen from accelerators, suppressors, levelers, and mixtures thereof.

8. The method of claim 1 wherein the impedance is selected at a frequency of 1 Hz.

9. The method of claim 1 wherein a plurality of frequencies is selected in step g).

* * * * *